(12) United States Patent
Shaver (10) Patent No.: US 7,501,645 B2
(45) Date of Patent: ***Mar. 10, 2009

(54) CORNEA CHARACTERISTICS MEASURING DEVICE

(75) Inventor: Jesse H. Shaver, Nashville, TN (US)

(73) Assignee: Campbell Science Group, Inc., Lenexa, KS (US)

( * ) Notice: Subject to any disclaimer, the term of this patent is extended or adjusted under 35 U.S.C. 154(b) by 27 days.

This patent is subject to a terminal disclaimer.

(21) Appl. No.: 11/560,184

(22) Filed: Nov. 15, 2006

(65) Prior Publication Data

US 2007/0091266 A1   Apr. 26, 2007

Related U.S. Application Data

(63) Continuation of application No. 10/685,886, filed on Oct. 15, 2003, now Pat. No. 7,154,111.

(51) Int. Cl.
*G01N 21/86* (2006.01)
*G01B 9/00* (2006.01)

(52) U.S. Cl. .......................... 250/559.27; 250/559.29; 356/125; 356/126

(58) Field of Classification Search ............ 250/559.16, 250/559.27, 559.29, 559.32, 559.49; 356/124, 356/125, 609; 606/5, 10, 405
See application file for complete search history.

(56) References Cited

U.S. PATENT DOCUMENTS

| | | | |
|---|---|---|---|
| 4,407,008 A | 9/1983 | Schmidt et al. | |
| 4,761,071 A | 8/1988 | Baron | |
| 4,805,971 A | * 2/1989 | Fantone ........................ | 359/354 |
| 4,806,004 A | 2/1989 | Wayland | |
| 4,817,432 A | 4/1989 | Wallace et al. | |
| 4,823,801 A | 4/1989 | Sakane | |

(Continued)

FOREIGN PATENT DOCUMENTS

DE    196 32 594 A1    2/1998

(Continued)

OTHER PUBLICATIONS

Cha et al., "Nontranslational three-dimensional profilometry by chromatic confocal microscopy with dynamically configurable micromirro scanning", Applied Optics, vol. 39, No. 16, pp. 2605-2613, Jun. 1, 2000.

(Continued)

*Primary Examiner*—Georgia Y Epps
*Assistant Examiner*—Don Williams
(74) *Attorney, Agent, or Firm*—Dicke, Billig & Czaja, PLLC (57) ABSTRACT

An apparatus for measuring characteristics of a substance is provided. The apparatus includes a light source to generate light to form an image. A splitter transmits the light from the light source to a first lens, which collimates the light. A second lens receives the collimated light and is adapted to oscillate with respect to the substance and adapted to transmit and focus the light to a focal region within the substance, such that the oscillation will cause the focal region to pass back and forth through the substance and its surfaces/interfaces. A sensor receives light reflected from the focal region and provides a signal indicative of characteristics of the substance at the focal region.

34 Claims, 5 Drawing Sheets

U.S. PATENT DOCUMENTS

| | | |
|---|---|---|
| 4,984,883 A | 1/1991 | Winocur |
| 5,239,178 A | 8/1993 | Derndinger et al. |
| 5,404,884 A | 4/1995 | Lempert |
| 5,491,524 A * | 2/1996 | Hellmuth et al. ............ 351/212 |
| 5,663,781 A | 9/1997 | Wilms et al. |
| 5,673,097 A | 9/1997 | Heacock |
| 5,760,950 A | 6/1998 | Maly et al. |
| 5,785,651 A | 7/1998 | Kuhn et al. |
| 5,861,955 A | 1/1999 | Gordon |
| 6,113,542 A | 9/2000 | Hyman et al. |
| 6,137,585 A | 10/2000 | Hitzenberger et al. |
| 6,193,371 B1 | 2/2001 | Snook |
| 6,275,718 B1 | 8/2001 | Lempert |
| 6,382,794 B1 | 5/2002 | Lai et al. |
| 6,585,723 B1 | 7/2003 | Sumiya |
| 6,626,895 B2 * | 9/2003 | Frey et al. ..................... 606/10 |
| 6,637,880 B1 | 10/2003 | Yamakaji et al. |
| 6,897,964 B2 | 5/2005 | Takahashi et al. |
| 2003/0058404 A1 | 3/2003 | Thorn et al. |

FOREIGN PATENT DOCUMENTS

| | | |
|---|---|---|
| EP | 0485803 A1 | 5/1992 |
| EP | 0810457 A1 | 12/1997 |
| GB | 2144537 A | 3/1985 |
| JP | 03055510 | 3/1991 |

OTHER PUBLICATIONS

Bohnke et al., "Continuous Non-contact Corneal Pachymetry with a High Speed Reflectometer", Journal of Refractive Surgery, vol. 14, pp. 140-146, Mar./Apr. 1998.

Pitris e tal., "A GRISM-based probde for spectrally encoded confocal microscopy" Optics Express, vol. 11, No. 2, pp. 120-124, Jan. 27, 2003.

ScienceDaily News Release: Adaptive Optics Technology Provides Powerful Tools for Eye Doctors, http://www.sciencedaily.com/releases/2002/06/020624072333.html, Jun. 24, 2002.

* cited by examiner

CORNEA CHARACTERISTICS MEASURING DEVICE

CROSS REFERENCE TO RELATED APPLICATION

The present application is a continuation of U.S. patent application Ser. No. 10/685,886, filed on Oct. 15, 2003, which is based on and claims the benefit of U.S. provisional patent application entitled "Cornea Thickness Measuring Device", Ser. No. 60/431,085, filed Dec. 5, 2002, and U.S. provisional patent application entitled "Cornea Characteristics Measuring Device", Ser. No. 60/418,958, filed Oct. 16, 2002, the contents of which are all hereby incorporated by reference in their entirety.

BACKGROUND

Measurements of characteristics of the eye are useful in providing appropriate eye care. For example, measurements of the eye have been useful in refractive surgical procedures, such as LASIK, wherein a portion of eye tissue is removed to enhance vision of a patient. Additionally, measurements are useful in studying the eye and diagnosing eye disorders.

In refractive surgical procedures, the thickness of the cornea is a valuable parameter in determining how much tissue of the eye should be removed. The thickness of the cornea is also valuable in diagnosis, prognosis, medical & surgical procedures, and monitoring of other conditions, such as glaucoma. Devices known as pachymeters (or alternatively pachometers) are used to measure the thickness of the cornea.

Corneal haze is another characteristic measured and used in the treatment and study of eyes. Corneal haze results from an alteration of corneal transparency, which may negatively impact vision. Many eye disorders such as macular corneal dystrophy, bullous keratopathy, keratoconus, lumican deficiency (in mice), fungal infection and endothelial injury are thought to contribute to corneal haze. Additionally, haze may form after surgical procedures or injuries.

One device that measures characteristics of the eye is an ultrasonic probe. Ultrasonic probes use sound waves to obtain measurement data, typically a measurement of the thickness of a cornea at a particular point. The probes generally contact the cornea during measurement, causing discomfort to the patient. Further, the measurement process using an ultrasonic probe may require several minutes if multiple measurements are necessary to achieve accurate results. The accuracy of ultrasonic pachymetry is also dependent upon accurate knowledge of the speed of sound in corneal tissue, which may range from 1200 to 2000 meters per second in different eyes. Finally, it is difficult to assure perpendicularity of the measurement axis to the corneal surface. Lack of perpendicularity may result in erroneously large measurements.

Another device that measures characteristics of the eye is a corneal confocal microscope. A confocal microscope illuminates a small region of a substance, such as a cornea, with a collimated light source focused through an objective lens to a tiny volume of space at the focal region of the lens. A detector that is "confocal" with the focal volume detects any backscattered or reflected light from the focal region. A viewable histological image is formed by a confocal microscope. One disadvantage of confocal microscopes is that they are extremely expensive and complex. Thus, confocal microscopes are not readily available to provide measurements of an eye. In addition, confocal microscopes are big, bulky devices that may be difficult to maintain, align, and transport. The confocal microscopes also cause patient discomfort due to the fact that the lens of the microscope contacts the cornea and the light source of the microscope is bright. The measurement time can last several minutes.

In a corneal confocal microscope, signals detected by the detector form images that may be analyzed to measure the thickness or opacity of the cornea and may further be used to generate a topographical or tomographical image of the cornea. Images taken of a cornea using a confocal microscope can also provide a visual representation of corneal haze.

As one might imagine, a system of quantification of corneal haze is useful in diagnosis and in assessment of various experimental treatments or prevention protocols. Many such methods for haze quantification have been developed. Clinically, haze is evaluated by "slitlamp" examination, ranked on a scale from 0 to 4 with 0 being normal and 4 being quite severe. However, this scale is subjective and only coarsely defines the amount of corneal haze.

As a result, it is desirable to have a low cost device that can measure various characteristics of the eye, such as thickness and haze. Furthermore, a standardization of corneal haze is desirable to further aid in experimentation, reporting, and analysis of corneal haze.

SUMMARY

An apparatus for measuring characteristics of a substance is provided. The apparatus includes a light source to generate light and a collimating lens to collimate the light. In one embodiment, a pattern of multiple measurement points are formed from the light. A filter such as a hologram or grating can be used to form an image of several points from the light via interference effects. An arrangement of pinholes can also be used to create a source image of multiple points for simultaneous measurement of multiple focal regions.

A fixed lens collimates light from the filter. An objective lens receives the collimated light and is adapted to focus light in an oscillatory manner. In one embodiment, the objective lens is adapted to oscillate with respect to the substance under analysis and to transmit and focus the light into the substance (or to the highly reflective surfaces and interfaces of the substance as scanning of the focal region proceeds). A portion of the light reflected from the focal region or regions in the substance is then effectively re-collimated by the objective lens and directed along the original path, in the reverse direction, then partially deflected (through use of a beam splitter or fiber-optic couplers). This reflected light provides a signal indicative of characteristics of the substance at the focal region (or focal regions, if a hologram and multi-sensor array are used to simultaneously analyze multiple points). The portion of the light reflected from points other than the focal region is rejected through use of an appropriate spatial filter, according to the confocal principle.

Also, as another aspect of the present invention, a method is provided for quantitatively measuring characteristics of a cornea. The method includes generating light and collimating the light with a first lens. The light from the first lens is focused into a focal region of the cornea with a second lens. A portion of light reflected from the focal region is sensed and a signal indicative of the portion of light reflected is provided.

To quantify corneal haze, a series of standard reference solutions having known turbidity values are measured with the device, with the known turbidity of each corresponding to the measured signal strength. Next, or in the alternative before the foregoing, a measurement of the turbidity of the cornea is taken using the same device under the same operational parameters in a timeframe in which the operational characteristics of the instrument may be assumed to be constant. After all measurements are taken, the measurements are analyzed and compared, and the turbidity of the cornea is assigned a value according to the appropriate interpolation of its signal strength compared to the standard turbidity scale from the standard solution measurements.

In yet another aspect of the present invention, a kit of secondary standards appropriate for the given device are provided so that correct instrumental calibration may be verified more conveniently in a setting less amenable to the primary standard, such as a clinic. The secondary standard kit samples may also serve as standards for characteristics other than haze, such as thickness. For example, plates may be of a certain thickness and/or opacity to provide simultaneous calibration for measurement of both properties.

DETAILED DESCRIPTION

Figure 1:
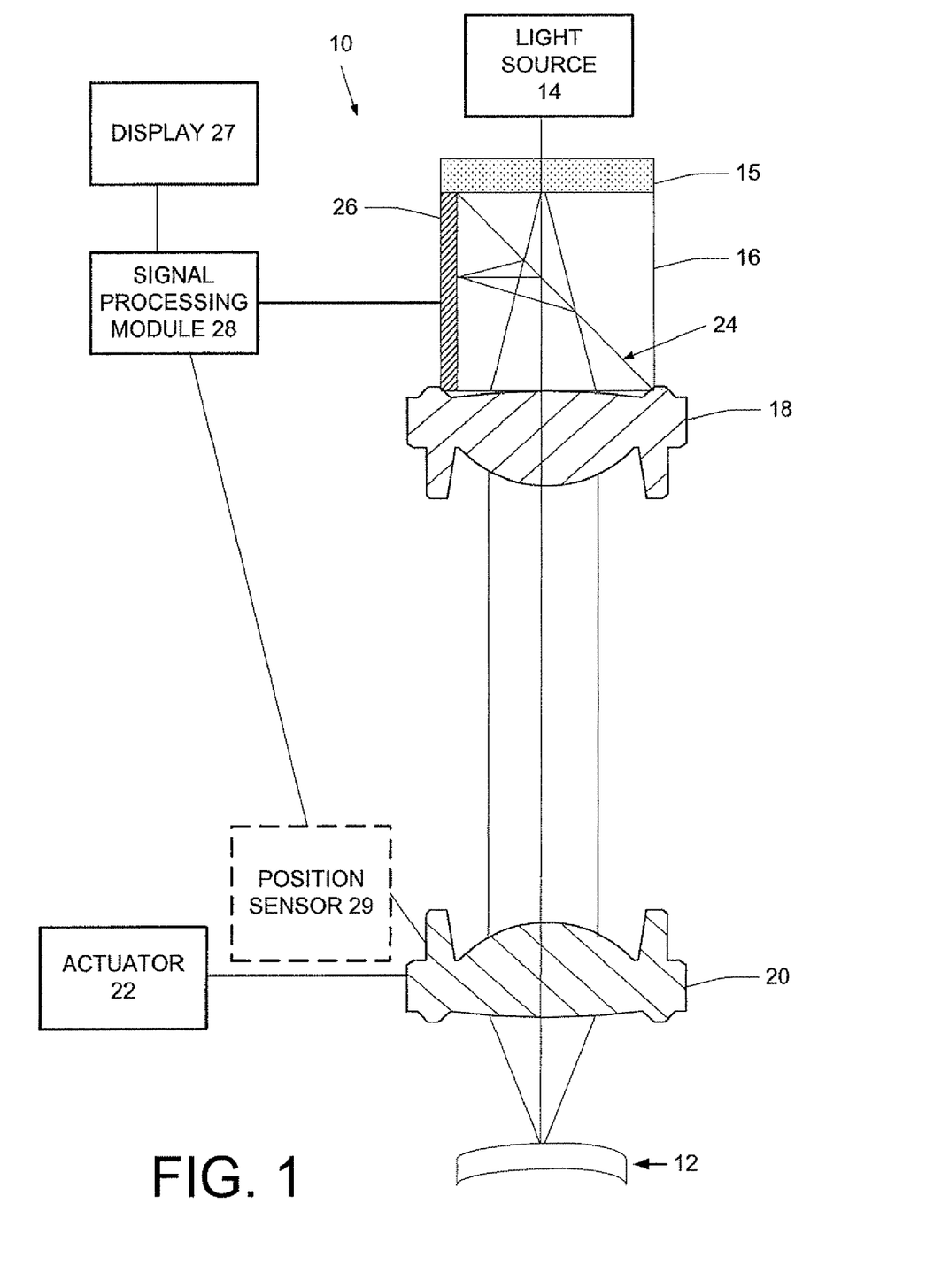
FIG. 1 is a schematic view of a device according to the present invention.

A device 10 as schematically illustrated in FIG. 1 can be assembled in order to provide a signal indicative of the thickness and/or opacity of a sample 12. Device 10 includes a light source 14 (herein a visible diode laser, but the light, which is defined herein broadly as electromagnetic radiation, could be visible and/or non-visible, coherent and/or non-coherent) that passes light first through a filter 15, such as a pinhole, hologram or other suitable means of image generation as necessary, to create an image (for example, three points arranged as the vertices of an equilateral triangle). Any type of image or number of focal spots can be used as discussed below. The light produced by light source 14 may be emitted from diode lasers, visible and/or white light emitting diodes or infrared emitting diodes, or traditional light bulbs, for example.

The light then passes through a splitter 16 that deflects a portion of the light. Splitter 16 illustratively may be a beam splitter cube, fiber optic coupler, or other component. Light that has passed un-deflected through splitter 16 then passes through a lens 18, which collimates the light and transmits it to scanning lens 20. Lens 20 may be the final objective lens, or merely the scanning element before a final objective lens. Actuator 22 is provided to actuate lens 20 such that a high number of measurements taken along the axis of motion may be obtained in a short time period and to focus light through the sample 12. In one embodiment, lens 20 is actuated in a direction toward (and away) from sample 12 along the axis of the collimated light beam.

It is worth noting that a stationary objective lens can also be used. In order to scan through the cornea, an objective lens with a high chromatic aberration characteristic should be used and the light source should provide light with varying frequencies that are refracted to different focal points in the sample. Additionally, a multi-element detector adapted to detect the light at different frequencies should be used. In an alternative embodiment, a grating-prism combination (known as GRISM) can be used to scan through the cornea.

Light that reflects from a focal region within sample 12 is reflected back to reflector 24 within splitter 16. Reflector 24 then reflects light onto sensor 26 to sense parameters of the reflected light. For example, sensor 26 can include an appropriately small active element or any detector or detector array with proper spatial filtering for the original light configuration from light source 14. Sensor 26 provides a signal (or signals) indicative of thickness and/or opacity of sample 12 to signal processing module 28. Signal processing module 28 calculates the thickness and/or opacity of sample 12 given the signals received from sensor 26. A display 27 or other rendering device can be coupled to the signal processing module 28 and is adapted to display an output of the calculation from signal processing module 28.

In one embodiment, the lens 18 and/or 20 is a plastic aspheric lens similar to those originally designed as a collimation and objective lens for diode laser sensing applications, particularly CD-ROM heads and laser pointers. A wide selection of low-cost plastic lenses are available. These lenses are helpful for two reasons. First, the low mass of the plastic lens enables high-frequency scanning, in the range of tens to hundreds of Hertz. This feature can be important in a hand-held device, since the measurements can be taken on a time scale where little relative movement occurs between the operator's hand, the instrument, and the cornea. Second, these optimized aspheric lenses have the high numerical apertures that provide successful confocal optical sectioning.

The axial resolution of confocal optics is largely governed by a characteristic of the lens known as the numerical aperture (NA). Any size NA may be used, although axial resolution may be compromised. With well-engineered detector circuitry, a lower NA lens may be used. A high NA lens provides increased resolution, although one drawback of high NA lenses is the shorter working distance (WD). In one embodiment, a device with an approximately 3 mm working distance can be achieved with a 0.47 NA lens, while an approximately 8.3 mm WD can be met with a 0.22 NA lens. This working distance is an improvement compared to contact ultrasound instruments, as well as current confocal instruments, which require much more complex objective lens assemblies to achieve their primary function, histologic imaging.

A suitable feedback mechanism can be employed in order to notify an operator of the device that the device is in a suitable range of operation corresponding to the working distance. For example, the feedback can be audio or visual based on the signals detected by sensor 26. Signal processing module 28 can provide appropriate feedback to the operator when reliable signals are received from sensor 26. If the object to be measured is outside the working distance of the device, unreliable or weak signals will be received by sensor 26.

In another embodiment of the present invention the objective tip of the instrument could be integrated into an applanation instrument for simultaneous or nearly simultaneous measurement of corneal thickness and intra-ocular pressure by a form of tonometry. Providing pressure and thickness measurements in the same instrument would save time and also aid in developing a correlation between pressure and thickness, particularly with regard to diseases such as glaucoma.

Figure 2:
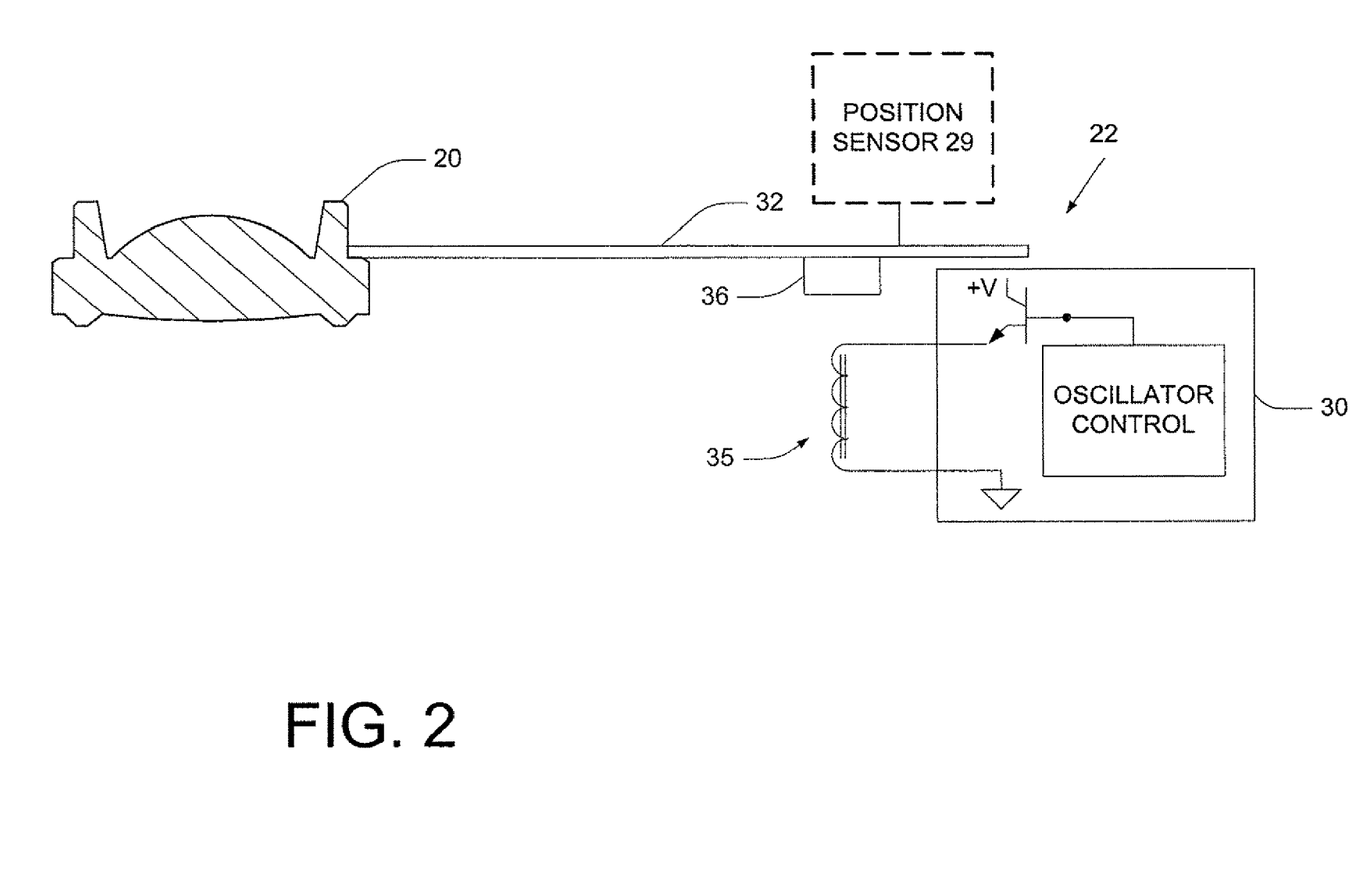
FIG. 2 is a schematic view of an actuator according to the present invention.

Actuator 22 can be a mechanical oscillator driven by an electronic circuit. In one embodiment, as illustrated in FIG. 2, the actuator 22 includes a drive circuit 30 that provides a signal to scan lens 20 at a rate of more than 100 Hz via electromagnetic force interaction. The speed of mechanical oscillation is governed by mechanical and physical characteristics of the scanning mechanism. Higher speeds are, in general, desirable, if the data acquisition system can support rapid detection. Drive circuit 30 includes an oscillator control, for example a 555 timer, and an output transistor to drive a coil 35. Alternatively, the oscillator control might provide an initial kicking impulse to the coil, and then rely on an electromagnetic triggering scheme incorporated into an armature coupled to the lens 20, to provide reliable, self-calibrated harmonic resonant oscillation. This scanning allows the device 10 to yield many data points in a short period of time (measured in seconds or fractions of a second). As lens 20 moves axially with respect to the collimated light, the focal point of the lens 20 moves throughout the sample 12.

As previously stated, the device is able to scan the objective lens 20 along the axial dimension at a frequency of tens to hundreds of Hz, over a distance of millimeters. This scanning is easily accomplished by mounting the lens 20 on an armature 32 such as a piece of spring-steel or similar material, and then "kicking" the oscillator at its natural frequency through use of an electromagnetic coil 35 driven by drive circuit 30 and an attached permanent magnet 36. Instead of a single armature, a design with multiple parallel armatures could be used to increase the linearity of the scanning translation motion. Alternatively, other spring types may be used, such as coil springs or bellows springs. Different spring geometry may be advantageous to alter scanning speed, device geometry, or the ease with which the device may be manufactured, assembled, and aligned. While other arrangements, such as a voice coil motor, a rotational motor and camshaft mechanism, or a piezoelectric actuator are possible, the spring scanning arrangement is simple and stable, similar to a tuning fork. It is simple and inexpensive to build the circuits to accomplish the scanning, as the components are largely similar to simple components found in audio circuits or electro-mechanical clocks. Audio signals have been used to find the resonance frequency of a particular arrangement, and simple square-wave oscillators have also been used. These circuits are based on a 555 timer IC and a small output transistor that controls current flow through the voice coil, but more sophisticated forms of pulse code modulation are possible. An electromagnetically-driven scanner has the advantage of cost, tunability, simplicity, reliability, speed, and low power consumption necessary for a hand-held device.

The physical position of the scanning armature 32 may either be monitored and recorded as a separate data track (via optical, magnetic, capacitive, Hall effect sensor, or any other means), or simply be a well-characterized motion achieved through precision manufacture and verified through measurement of an object of known thickness. A suitable position sensor 29 may be provided to measure the position of lens 20 and provide an output indicative of a position of lens 20 to signal processing module 28. When device 10 scans through the sample 12, in particular a cornea, regions corresponding to front and back surfaces are bright and reflective. Images received by sensor 26 correspond to different brightness values.

Figure 3:
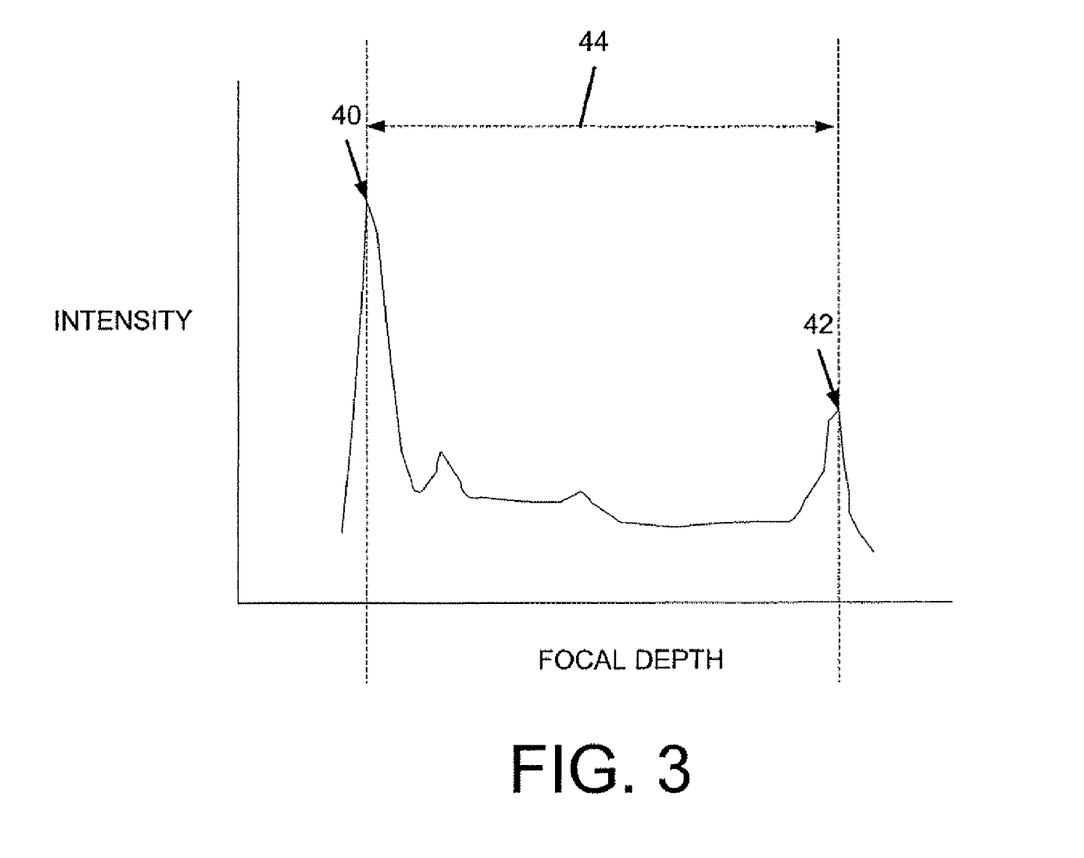
FIG. 3 is a plot of various measurements taken of a cornea.

When the value or values are plotted as a function of focal depth, a characteristic curve as illustrated in FIG. 3 results. The curve can be representative of a single scan or multiple scans that are averaged. In FIG. 3, both the epithelium (the outermost layer of cells of the cornea) and endothelium (the innermost layer of the cornea) produce relatively large peaks, illustrated as peaks 40 and 42, respectively. A distance 44 between peaks 40 and 42 provides an accurate measurement of corneal thickness when the movement and optical characteristics of the scanning mechanism that generated the signal are known. In one embodiment, signal processing module 28 is a computer that includes an algorithm to compute the height and position of the peaks. The signal processing module 28 may provide results on display 27. As appreciated by those skilled in the art, analog circuitry or combinations of analog and digital circuitry can be used for signal processing and pre-processing. Furthermore, signal processing module 28 may be embodied in a conventional computing environment that collects, stores and analyzes signals received from sensor 26.

If desired, an arrangement of three or more fiber optic tips may be used as light source 14, which creates three or more signals. A similar image may be achieved with a hologram or a pinhole array. For example, a light delivery system with a fiber optic tip serves as both the light source 14 and the sensor 26. The fiber optic tip as light source 14 and sensor 26 provides a rugged, self-aligned design, and the beam splitter may also be replaced by a fused fiber coupler in this embodiment. In one embodiment, a multimode fiber having a 62 micron core is used. Another embodiment uses a single mode fiber having an 8 micron core.

Figure 4:
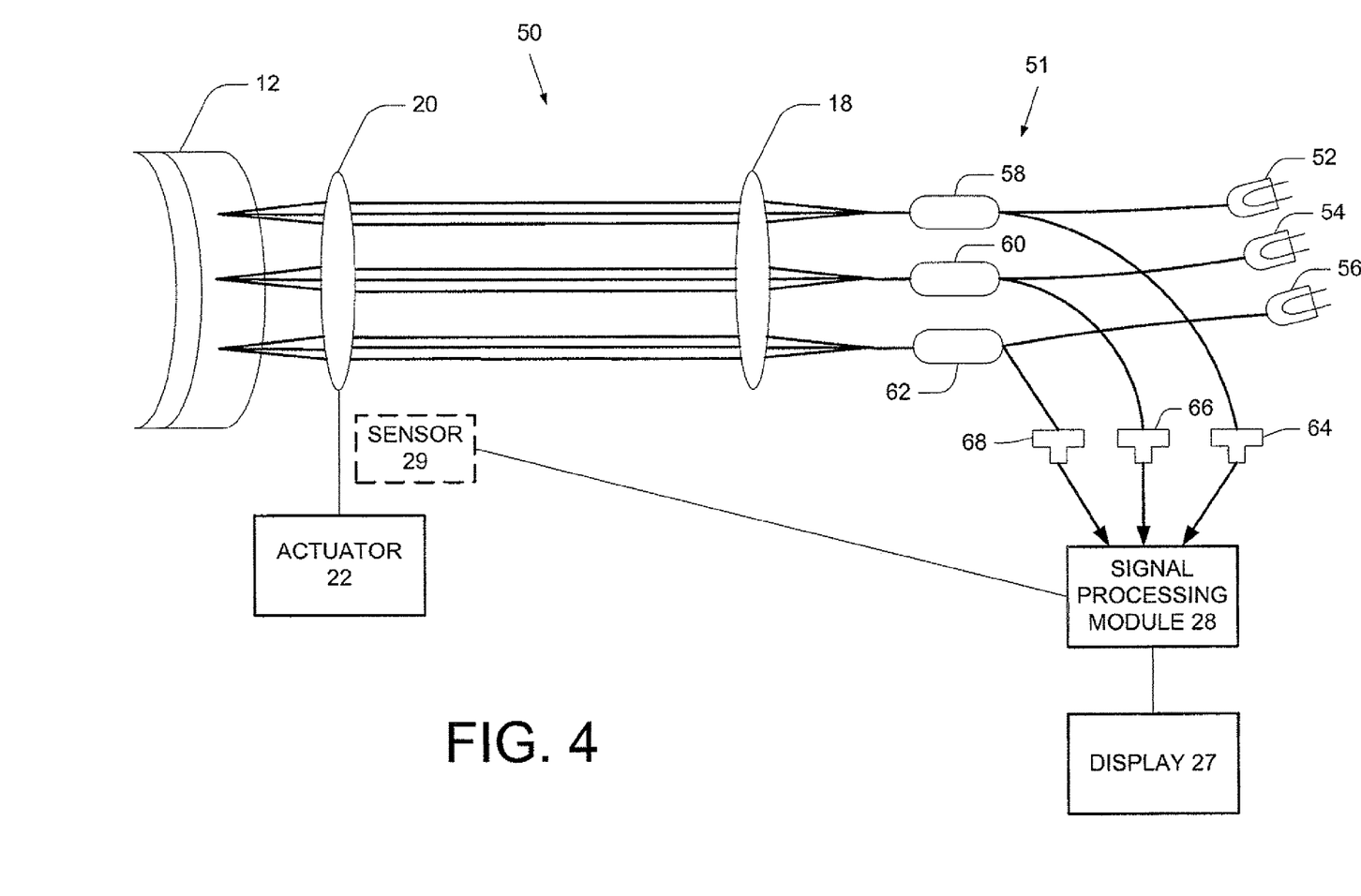
FIG. 4 is a schematic view of an alternative embodiment of the present invention.

FIG. 4 illustrates a schematic view of a device 50 using a fiber optic coupler 51 as the light source and detector. In one embodiment, a fused fiber optic coupler can self-align the light source and detector in a single component to assure that the light source and detector are confocal. A rugged, single component additionally prevents disruption of the alignment during operation. Components in FIG. 1 are similarly numbered in FIG. 4. In the embodiment illustrated, three fiber-coupled laser diodes 52, 54, 56 emit light to three 2×1 fiber splitters 58, 60 and 62, respectively. Undeflected light from splitters 58, 60 and 62 is passed through fibers (which serve as pinholes) to fixed lens 18. Light from the splatters are focused on three spots (that can form apices of an equilateral triangle) within sample 12, while lens 20 focuses the focal spots through sample 12. Light reflected from sample 12 is detected by three fiber-coupled photo detectors 64, 66 and 68 coupled to splitters 58, 60 and 62, respectively. The photo detectors 64, 66 and 68 provide signals to signal processing module 28. A relative phase error between return signals sensed by the detectors can be used to determine the angle at which device 50 is held. Calculations can then be made by signal processing module 28 to correct for the angle at which the device 50 is held.

Figure 5:
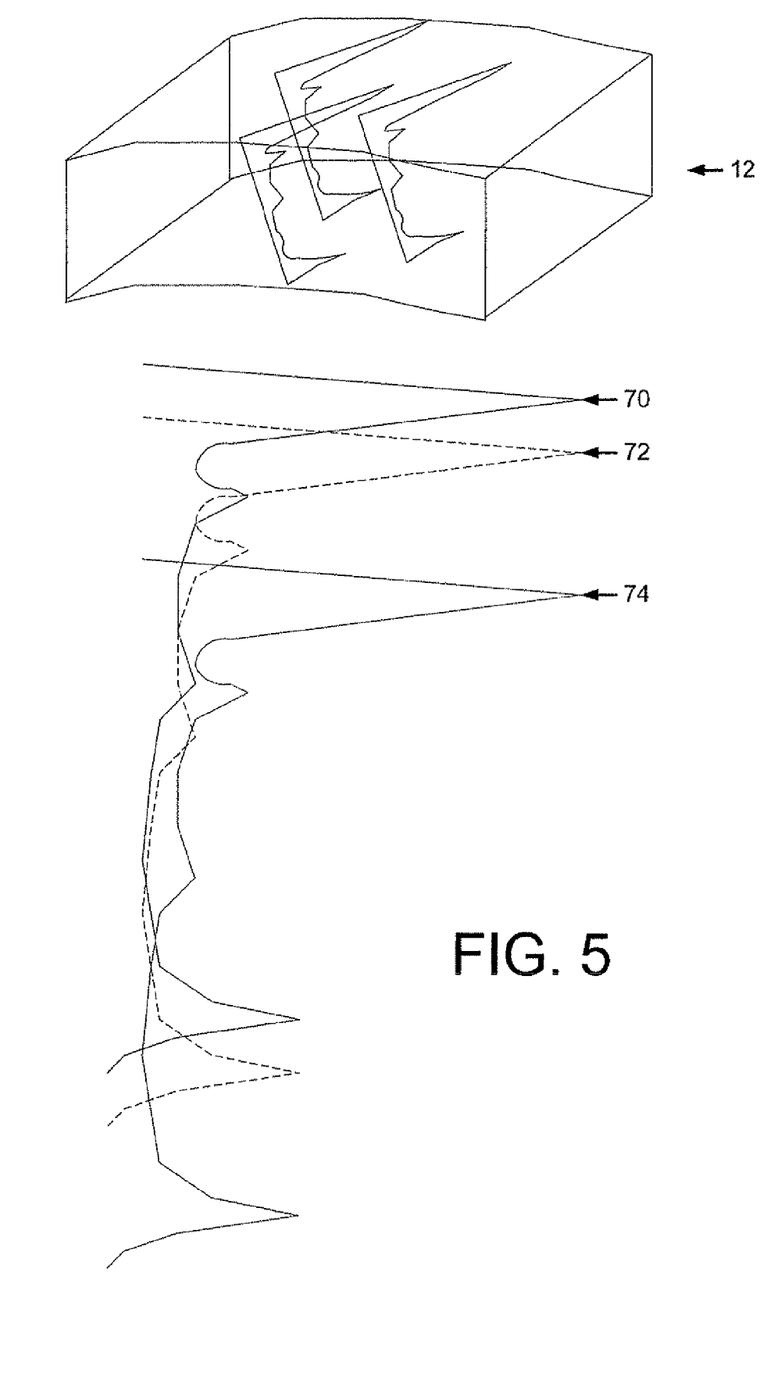
FIG. 5 is a diagram of a plurality of measurements taken of a cornea.

Three-dimensional multiple point measurement (3d Triangulation) is an advantage over ultrasound technology. Instead of simply using one focal spot, three or more focal spots can be synchronously focused in an oscillatory manner through the cornea. Three plots (70, 72 and 74) are shown in FIG. 5, as might be generated by oscillating the three focal spots through sample 12 at a skewed angle relative to the surface normal vector. The optics are such that the spots form the apices of an equilateral triangle in three dimensional space, thereby defining a plane. If the axis of the objective scanning is normal (perpendicular) to the plane of the cornea, the three signals will be in phase. If, however, the probe is not in perfect alignment (as one might expect in a hand-held device), a simple trigonometric equation allows the device to calculate the angle at which the probe is held using the phase error of the three signals (appropriately mapped back to Cartesian space according to their motion characteristics) and the known spacing of the focal points in three dimensional space, which then further allows the proper corneal thickness to be calculated.

Ultrasound probes suffer from the fact that misalignment during measurement can yield widely varying results. In order to create the "three spot pattern" or some similar illumination geometry, one may employ either common gratings or a computed or traditionally generated holographic mask. Such technology is inexpensive, and would result in clean patterns while minimizing the "wasted light" from the light source. Computed holographic masks could easily form greater than ½ the beam energy into three perfectly spaced spots, or some other suitable geometry. If a "custom mask" is prohibitively expensive, two perpendicular gratings may be used to create a 3×3 grid pattern, and similar results achieved with a modified algorithm. Finally, a hologram laser, which is an integrated optical device used in optical data readers consisting of a diode laser, hologram image formation component, beam splitter, and light sensor, could be used to consolidate various separate components of the device and reduce the size of the device and reduce the cost associated with alignment difficulty of the various components.

It will further be appreciated that the intensity of signals received from a sample 12 can be interpreted as a measurement of turbidity of the sample, which can be compared to a measurement of a standard material to quantify an amount of haze present in a cornea. Healthy corneas are quite transparent and only scatter approximately 2% to 10% of incident light across the visible spectrum. Corneal haze is thought to be the result of incongruities in the cornea, which causes an increase in the amount of scattered light in the cornea. Referring to FIG. 3, the relative intensity of data points between peak 40 and 42 may be extracted in order to provide a relative measurement of the turbidity of sample 12. The relative measurement can be compared to a substance having a known turbidity. As a result of the comparison, a quantified measurement of haze in sample 12 results. Accordingly, an objective quantified value of haze can be determined.

A standardized substance may be used having a known turbidity to calibrate devices 10 and 50. For example, a set of calibrating plates having known turbidity values can be used to perform the calibration. After calibration has been performed, signal processing module 28 can interpret signals received from devices 10 and 50 in order to provide a relative output using values obtained from the calibration plate. Calibration of thickness measurement may also be achieved by using a substance (such as a plate) having a known thickness. A kit including several reference plates of known parameters such as opacity and thickness is useful in providing an easy way to calibrate devices 10 and 50.

In one embodiment, a calibrated reference solution such as formazin polymer suspension of known concentration is measured with the instrument, and this measurement is then compared to measurements of the cornea to provide reproducible results of the amount of haze in a cornea. Varying amounts of formazin turbidity may be used as reference values to quantify corneal range. For example a range of 0-4000 Nephelometric Turbidity Units (NTU) for formazin may be used as a primary standard in the development of a secondary standard of haze measurements.

Although the present invention has been described with reference to preferred embodiments, workers skilled in the art will recognize that changes may be made in form and detail without departing from the spirit and scope of the invention.

What is claimed is:

1. An apparatus for measuring characteristics of a substance, comprising:
    a light source to generate light;
    means for collimating the light in a direction toward the substance along an axis;
    means for scanning an objective lens along the axis to focus the light toward the substance;
    means for monitoring a position of the objective lens;
    means for detecting light reflecting off of the substance that is confocal with the focal region; and
    means for providing a signal indicative of characteristics of the substance as a function of detected light and the position of the objective lens.

2. The apparatus of claim 1 and further comprising means for calculating a thickness of the substance.

3. The apparatus of claim 2 wherein the means for detecting are adapted to determine a first surface of the substance at a first position along the axis and a second surface of the substance at a second position along the axis and wherein the means for calculating are adapted to determine a distance between the first position and the second position.

4. The apparatus of claim 1 and further comprising means for calculating an opacity of the substance.

5. The apparatus of claim 1 wherein the means for collimating includes a collimating lens to collimate the light.

6. The apparatus of claim 1 and further comprising means for filtering the light to form an image pattern.

7. The apparatus of claim 1 wherein the light source is a laser.

8. The apparatus of claim 1 and further comprising:
    a display to display the signal.

9. A corneal pachymeter measuring characteristics of a cornea, comprising:
    a light source to generate light;
    a first lens collimating the light in a direction along an axis;
    a second lens positioned along the axis and focusing the light to a focal region;
    an actuator operably coupled to the second lens to oscillate the second lens along the axis;
    a position sensor operably coupled to the second lens to sense a position of the second lens; and
    a sensor receiving the light reflected from the focal region and providing a signal indicative thereof as a function of the position of the second lens.

10. The pachymeter of claim 9 and further comprising a signal processing module receiving the signal from the sensor and providing an output indicative of properties of the substance at said focal region.

11. The pachymeter of claim 10 wherein the output is indicative of at least one of a thickness and an opacity of the cornea.

12. The pachymeter of claim 9 and further comprising a filter to form an image pattern of light from the light source.

13. The pachymeter of claim 12 wherein the image pattern includes at least three focal spots, spaced apart from one another.

14. The pachymeter of claim 13 wherein the sensor receives light indicative of the at least three focal spots and wherein a signal processing module is coupled to the sensor and calculates a relative phase difference of signals associated with each of the at least three spots and provides an output indicative thereof.

15. The pachymeter of claim 14 wherein the at least three focal spots are focused into the cornea.

16. The pachymeter of claim 9 wherein at least one of the first lens and the second lens is a plastic aspheric lens.

17. The pachymeter of claim 9 wherein the direction is toward the cornea.

18. The pachymeter of claim 9 and further comprising:
    a signal processing module coupled to the sensor and the position sensor and adapted to determine a first surface of the cornea, a second surface of the cornea and a distance between the first surface and the second surface as a function of the position of the lens.

19. A method of measuring characteristics of a substance, comprising:
    generating light;
    collimating the light with a first lens in a direction toward the substance along an axis;

focusing the light with a second lens into a focal region of the substance;

oscillating the second lens along the axis to focus the light into the substance;

sensing a position of the second lens;

sensing a portion of light reflected from the focal region of the substance; and providing a signal indicative of the portion of light reflected as a function of the position of the second lens.

20. The method of claim 19 and further comprising providing a feedback signal indicative of an acceptable working distance between the second lens and the cornea.

21. The method of claim 20 and further comprising displaying the signal indicative of the portion of light reflected.

22. The method of claim 20 wherein the substance is a cornea.

23. The method of claim 20 wherein the signal is indicative of a thickness of the cornea.

24. The method of claim 23 and further comprising:

sensing a portion of light reflected from a first surface of the cornea at a first position along the axis;

sensing a portion of light reflected from a second surface of the cornea at a second position along the axis further away from the first lens than the first position; and calculating the thickness of the cornea based on a distance between the first surface and the second position along the axis.

25. The method of claim 23 and further comprising comparing the signal to a reference signal indicative of a known thickness.

26. The method of claim 20 wherein the signal is indicative of an opacity of the cornea.

27. The method of claim 26 and further comprising comparing the signal to a reference signal indicative of a known opacity.

28. The method of claim 20 and further comprising filtering the light to form an image pattern of light.

29. The method of claim 28 wherein the image pattern includes at least three focal spots, spaced apart from one another.

30. The method of claim 29 and further comprising receiving reflected light indicative of at least three focal spots and calculating a relative phase difference of signals associated with each of the at least three spots.

31. The method of claim 20 and further comprising partially deflecting light and reflecting light from the focal region with a beam splitter.

32. The method of claim 20 and further comprising partially deflecting light and reflecting light from the focal region with a fiber optic coupler.

33. The method of claim 20 wherein the second lens is a plastic lens.

34. The method of claim 33 wherein the second lens has a numerical aperture in a range from approximately 0.47 to approximately 0.22.

* * * * *